United States Patent [19]
Otsuka et al.

[11] Patent Number: 5,965,779
[45] Date of Patent: Oct. 12, 1999

[54] FLUOROOXETANE COMPOUND AND PROCESS FOR ITS PREPARATION

[75] Inventors: Tatsuya Otsuka; Hirokazu Aoyama, both of Settsu, Japan

[73] Assignee: Daikin Industries, Ltd., Osaka, Japan

[21] Appl. No.: 09/027,251

[22] Filed: Feb. 20, 1998

[30] Foreign Application Priority Data

Feb. 21, 1997 [JP] Japan ................................ 9-037850

[51] Int. Cl.$^6$ ........................................ C07C 41/00
[52] U.S. Cl. ........................ 568/677; 568/669; 568/681; 568/683
[58] Field of Search .................... 568/677, 669, 568/681, 683

[56] References Cited

U.S. PATENT DOCUMENTS 4,946,972   8/1990   Ohsaka et al. ..................... 568/677

FOREIGN PATENT DOCUMENTS 0037850   2/1997   Japan .

*Primary Examiner*—Louise N. Leary
*Attorney, Agent, or Firm*—Larson & Taylor

[57] ABSTRACT

The present invention provides processes for preparing 2,2,3,3,4-pentafluorooxetane and/or 2,2,3,3,4,4-hexafluorooxetane which comprises reacting 2,2,3,3-tetrafluorooxetane with fluorine gas, the process inhibiting decomposition of the oxetane ring during the reaction and producing a reduced amount of by-products.

6 Claims, No Drawings

FLUOROOXETANE COMPOUND AND PROCESS FOR ITS PREPARATION

FIELD OF THE INVENTION

The present invention relates to 2,2,3,3,4-pentafluorooxetane, processes for its preparation, and processes for preparing 2,2,3,3,4,4-hexafluorooxetane. 2,2,3,3,4-Pentafluorooxetane and 2,2,3,3,4,4-hexafluoro-oxetane are useful as intermediates for pharmaceuticals or agricultural chemicals, or in place of perfluorocarbons (PFC) as dry etching gases.

BACKGROUND OF THE INVENTION

Various PFC are conventionally used as dry etching gases. However, since PFC are very stable in the atmosphere and high in global warming coefficient, emission of PFC is required to be reduced in amount. Recently, fluoroether compounds attract attention as dry etching gases. Among fluoroether compounds, fluorine-containing oxetanes are considered advantageously usable as dry etching gases since they easily decompose in the atmosphere because of their chemically unstable four-member ring structure.

A process for synthesizing 2,2,3,3,4,4-hexafluorooxetane, one of the fluorine-containing oxetanes, is disclosed in German Patent No. 814002. The process comprises electrolytically fluorinating an oxetane in hydrogen fluoride. The process, however, is not satisfactory since the oxetane easily decomposes during the reaction, producing a large amount of by-products.

A number of researches have been made on hydrogen-fluorine substitution reaction of organic compounds using fluorine gas (e.g., Lagow et al., J. Org. Chem., 42, 3437 (1977)). However, known processes require special reactors since fluorine is highly reactive and may cause a runaway reaction or explosion. Further, they require a low reaction temperature of −78° C. and a large amount of diluent gas in order to prevent side reactions such as cleavage of the carbon-carbon bond of the organic compound. Thus, known processes are not satisfactory for industrial purposes.

SUMMARY OF THE INVENTION

An object of the present invention is to provide a process for preparing 2,2,3,3,4-pentafluorooxetane and/or 2,2,3,3,4,4-hexafluorooxetane, which inhibits decomposition of the oxetane ring during the reaction and producing a reduced amount of by-products.

The present inventors carried out extensive research on industrially applicable processes for preparing 2,2,3,3,4-pentafluorooxetane (hereinafter sometimes referred to as "PFO") and/or 2,2,3,3,4,4-hexafluorooxetane (hereinafter sometimes referred to as "HFO"). They found that PFO and/or HFO can be prepared by reacting 2,2,3,3-tetrafluorooxetane (hereinafter sometimes referred to as "TFO") with fluorine gas.

The starting material, TFO, is a highly heat decomposable compound and fluorine gas is a highly reactive reagant. According to the present invention, however, the reaction of TFO with fluorine gas yields PFO and/or HFO with a good selectivity, without decomposition of TFO.

The present invention provides the following fluorooxetane and processes for preparing fluorooxetanes.

1. 2,2,3,3,4-Pentafluorooxetane represented by the formula

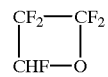

(1)

2. Process for preparing 2,2,3,3,4-pentafluorooxetane and/or 2,2,3,3,4,4-hexafluorooxetane, the process comprising reacting 2,2,3,3-tetrafluorooxetane with fluorine gas.
3. The above process 2 wherein the reaction is carried out in a liquid phase in the presence of a solvent inert to fluorine gas.
4. The above process 2 wherein the reaction is carried out in a gas phase in the presence of a diluent gas inert to fluorine gas.
5. The above process 3 wherein the solvent inert to fluorine gas is at least one member selected from the group consisting of perfluoroalkanes, chlorofluoroalkanes, perfluoropolyethers and anhydrous hydrogen fluoride.
6. The above process 4 wherein the diluent gas inert to fluorine gas is at least one member selected from the group consisting of nitrogen, helium, anhydrous hydrogen fluoride and perfluoroalkanes having 4 or less carbon atoms.

2,2,3,3,4-Pentafluorooxetane described in the above item 1 is a novel compound which has not been disclosed in any literature.

DETAILED DESCRIPTION OF THE INVENTION

In the process of the invention, 2,2,3,3-tetrafluorooxetane synthesized by the process disclosed in J. Org. Chem. 28 492 (1963) is used.

The reaction in the process of the invention can be carried out either in a liquid phase in the presence of a solvent inert to fluorine gas, or in a gas phase in the presence of a diluent gas inert to fluorine gas.

For carrying out a liquid phase reaction, TFO is brought into contact with fluorine gas preferably in the presence of at least one solvent inert to fluorine gas. Examples of the solvent inert to fluorine gas include, but are not limited to, anhydrous hydrogen fluoride; perfluoroalkanes such as perfluorocyclobutane, perfluorohexane, perfluorooctane and perfluorodecane; perfluoropolyether oils as shown in "Junkatsu (Lubrication)", vol.32, no.2, p.107 (such as "Demnum" manufactured by Daikin Industries, Ltd., "Fomblin" manufactured of Ausimont K.K., "Krytox" manufactured by Du Pont); chlorofluoroalkanes such as chlorotrifluoroethylene oligomeric oils as shown in "Junkatsu (Lubrication)" vol. 32, no.2, p.107 (such as CTFE oil manufactured by Daikin Industries, Ltd.); and the like. The perfluoropolyether oils and chlorotrifluoroethylene oligomeric oils are fluorine-based synthetic lublicants.

In addition to the above solvents, chlorofluorocarbons (e.g., CFC-113) can be used. However, use thereof should be avoided, since they destroy the ozone layer in the stratosphere when leaked into the atmosphere.

Fluorine gas can be fed into the reaction system by itself or as diluted with an inert gas such as nitrogen.

The reaction can be suitably carried out by a semi-batch process comprising placing at least one of the above solvents in a reactor, dissolving TFO thereto and blowing fluorine gas into the solution, or by a continuous process comprising placing at least one of the above solvents in a reactor and continuously feeding TFO and fluorine gas into the solvent.

The reaction temperature may be −20° C. to 100° C., and is preferably −10° C. to 30° C., more preferably −10° C. to the boiling point of TFO (28° C.). When the solvent used has a boiling point lower than that of TFO, it is necessary to provide the reactor with a condenser for preventing the solvent from flowing out of the reaction system.

The reaction is preferably carried out usually at atmospheric pressure. In some cases, however, it may be carried out under reduced pressure or under a slight pressure.

For synthesizing PFO selectively, it is preferable that a small amount of fluorine gas is reacted with excess TFO (TFO:$F_2$=1:1 to 5:1 (mole ratio)) for reducing the conversion degree of TFO and that produced PFO is successively removed from the reaction system. For synthesizing HFO selectively, it is preferable to carry out the reaction by a continuous process using fluorine gas in a sufficient amount relative to TFO (TFO:$F_2$=1:2 to 1:3 (mole ratio)).

When a gas phase reaction is carried out, it is essential to dilute fluorine gas with nitrogen, helium, anhydrous hydrogen fluoride, a perfluoroalkane having 4 or less carbon atoms, or like inert gas, in order to prevent a runaway reaction. The proportion of fluorine gas to the inert gas is preferably 5 to 20%. Fluorine gas is mixed with the inert gas preferably before being fed into the reaction system.

The reaction temperature is usually 30° C. to 250° C., preferably 50° C. to 150° C.

The reaction is preferably carried out usually at atmospheric pressure, but in some cases, it may be carried out under reduced pressure or under a slight pressure.

For synthesizing PFO selectively, a preferable mole ratio of TFO to $F_2$ is 1:1 to 5:1. For synthesizing HFO selectively, a preferable mole ratio of TFO to $F_2$ is 1:2 to 1:3.

The reaction can be carried out in the presence of a metal such as iron, copper, zinc, nickel, tin, chromium or the like, or a mixture and/or alloy of two or more of these metals. The metal may be placed in the reaction tube as a catalyst, or a reaction tube made of the metal may be used. Use of a thin tube accelerates heat removal and inhibits decomposition of the product.

The thus obtained PFO and HFO can be easily isolated by a conventional process such as rectification.

The present invention provides a process for preparing 2,2,3,3,4-pentafluorooxetane and/or 2,2,3,3,4,4-hexafluorooxetane, the process inhibiting decomposition of the oxetane ring during the reaction and producing a reduced amount of by-products.

BEST MODE FOR CARRYING OUT THE INVENTION

The following Examples illustrate the present invention in further detail.

EXAMPLE 1

A 200-ml stainless steel container provided with an inlet into the liquid phase and a gas outlet was charged with 146.1 g of chlorotrifluoroethylene oligomeric oil (CTFE oil #0 manufactured by Daikin Industries, Ltd.) and 43 g of 2,2,3,3-tetrafluorooxetane. While stirring the solution at room temperature, nitrogen gas (60 ml/min) and fluorine gas (6 ml/min) were mixed together and fed into the solution. The reaction was carried out constantly at atmospheric pressure. The discharged gas was washed with an alkaline aqueous solution and analyzed by gas chromatography.

The analysis revealed that the conversion degree of 2,2,3,3-tetrafluorooxetane was 9.8%, and that 2,2,3,3,4-pentafluorooxetane and 2,2,3,3,4,4-hexafluoro-oxetane were obtained with selectivities of 92.6% and 1.9%, respectively.

The product was rectified to isolate 2 g of 2,2,3,3,4-pentafluorooxetane. The structure of 2,2,3,3,4-pentafluorooxetane was confirmed by GC mass spectrum. The spectrum is shown below.

MS (70eV)m/e:101(M-COF, 21.2), 100 (79.2), 82(27.2), 69(21.2), 51(81.2), 50(25.6), 47(33.6), 31 (100), 29 (75.6)

EXAMPLE 2

A 200-ml stainless steel container provided with an inlet into the liquid phase and a gas outlet was charged with 150.0 g of perfluoropolyether oil ("Demnum S-20" manufactured by Daikin Industries, Ltd.) and 45 g of 2,2,3,3-tetrafluorooxetane. While stirring the solution at 10° C., nitrogen gas (60 ml/min) and fluorine gas (6 ml/min) were mixed together and fed into the solution. The reaction was carried out constantly at atmospheric pressure. The discharged gas was washed with an alkaline aqueous solution and analyzed by gas chromatography.

The analysis revealed that the conversion degree of 2,2,3,3-tetrafluorooxetane was 10.2%, and that 2,2,3,3,4-pentafluorooxetane and 2,2,3,3,4,4-hexafluoro-oxetane were obtained with selectivities of 93.5% and 1.3%, respectively.

EXAMPLE 3

820 g of anhydrous hydrogen fluoride was placed in a 1-liter still column provided with inlets into the liquid phase and gas phase and a condenser. While refluxing the hydrogen fluoride with heating at 20° C. at atmospheric pressure, fluorine gas (60 ml/min) and 2,2,3,3-tetrafluorooxetane (30 ml/min) were concurrently fed into the liquid phase and gas phase, respectively. After continuing the reaction for 3 hours, the reaction mixture was washed with an alkaline solution and analyzed by gas chromatography.

The analysis revealed that the conversion degree of 2,2,3,3-tetrafluorooxetane was 57%, and that 2,2,3,3,4-pentafluorooxetane and 2,2,3,3,4,4-hexafluoro-oxetane were obtained with selectivities of 92% and 7.3%, respectively.

EXAMPLE 4

824 g of anhydrous hydrogen fluoride was placed in a 1-liter still column provided with inlets into the liquid phase and gas phase and a condenser. While refluxing the hydrogen fluoride with heating at 20° C. at atmospheric pressure, fluorine gas (60 ml/min) and 2,2,3,3-tetrafluorooxetane (30 ml/min) were concurrently fed into the liquid phase and gas phase, respectively. After continuing the reaction for 3 hours, feeding of 2,2,3,3-tetrafluorooxetane was stopped, and fluorine gas alone was fed for further 3 hours at a rate of 20 ml/min. After completion of the reaction, the reaction mixture was washed with an alkaline solution and analyzed by gas chromatography.

The analysis revealed that the conversion degree of 2,2,3,3-tetrafluorooxetane was 95%, and that 2,2,3,3,4-pentafluorooxetane and 2,2,3,3,4,4-hexafluoro-oxetane were obtained with selectivities of 14% and 82%, respectively.

EXAMPLE 5

830 g of perfluorocyclobutane was placed in a 1-liter still column provided with inlets into the liquid phase and gas phase and a condenser. While refluxing the perfluorocyclobutane with heating at 20° C. at atmospheric pressure, fluorine gas (60 ml/min) and 2,2,3,3-tetrafluorooxetane (30 ml/min) were concurrently fed into the liquid phase and gas phase, respectively. After continuing the reaction for 3 hours, the reaction mixture was washed with an alkaline solution and analyzed by gas chromatography.

The analysis revealed that the conversion degree of 2,2,3,3-tetrafluorooxetane was 53%, and that 2,2,3,4-pentafluorooxetane and 2,2,3,3,4,4-hexafluoro-oxetane were obtained with selectivities of 93% and 6.5%, respectively.

EXAMPLE 6

A nickel reaction tube (¼ inch in outer diameter, 4 m in length, 56 ml in internal volume) was placed in a constant temperature tank and heated to 50° C. Fluorine gas (20 ml/min), nitrogen gas (100 ml/min) and 2,2,3,3-tetrafluorooxetane (10 ml/min) were passed through the reaction tube. Fluorine gas was mixed with nitrogen gas before the reaction, and the gas mixture was mixed with TFO in the constant temperature tank.

The discharged gas was washed with an alkaline aqueous solution and analyzed by gas chromatography.

The analysis revealed that the conversion degree of 2,2,3,3-tetrafluorooxetane was 66%, and that 2,2,3,3,4-pentafluorooxetane and 2,2,3,3,4,4-hexafluoro-oxetane were obtained with selectivities of 91.2% and 8.0%, respectively.

EXAMPLE 7

A nickel reaction tube (¼ inch in outer diameter, 4 m in length, 56 ml in internal volume) was placed in a constant temperature tank and heated to 150° C. Fluorine gas (24 ml/min), nitrogen gas (400 ml/min) and 2,2,3,3-tetrafluorooxetane (10 ml/min) were passed through the reaction tube. Fluorine gas was mixed with nitrogen gas before the reaction, and the gas mixture was mixed with TFO in the constant temperature tank.

The discharged gas was washed with an alkaline aqueous solution and analyzed by gas chromatography.

The analysis revealed that the conversion degree of 2,2,3,3-tetrafluorooxetane was 98%, and that 2,2,3,3,4-pentafluorooxetane and 2,2,3,3,4,4-hexafluoro-oxetane were obtained with selectivities of 15.4% and 80.5%, respectively.

We claim:

1. 2,2,3,3,4-Pentafluorooxetane represented by the formula

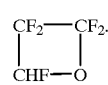

(1)

2. A process for preparing 2,2,3,3,4-pentafluorooxetane and/or 2,2,3,3,4,4-hexafluorooxetane, the process comprising reacting 2,2,3,3-tetrafluorooxetane with fluorine gas.

3. The process according to claim 2 wherein the reaction is carried out in a liquid phase in the presence of a solvent inert to fluorine gas.

4. The process according to claim 2 wherein the reaction is carried out in a gas phase in the presence of a diluent gas inert to fluorine gas.

5. The process according to claim 3 wherein the solvent inert to fluorine gas is at least one member selected from the group consisting of perfluoroalkanes, chlorofluoroalkanes, perfluoropolyethers and anhydrous hydrogen fluoride.

6. The process according to claim 4 wherein the diluent gas inert to fluorine gas is at least one member selected from the group consisting of nitrogen, helium, anhydrous hydrogen fluoride and perfluoroalkanes having 4 or less carbon atoms.

* * * * *